United States Patent [19]

Holla et al.

[11] Patent Number: 5,262,312
[45] Date of Patent: Nov. 16, 1993

[54] PROCESS FOR THE GLYCOSIDASE-CATALYZED SYNTHESIS OF GLYCO CONJUGATES

[75] Inventors: Wolfgang Holla, Hofheim/Taunus; Manfred Schudok, Frankfurt, both of Fed. Rep. of Germany

[73] Assignee: Hoechst Aktiengesellschaft, Frankfurt, Fed. Rep. of Germany

[21] Appl. No.: 689,480

[22] Filed: Apr. 23, 1991

[30] Foreign Application Priority Data

Apr. 25, 1990 [DE] Fed. Rep. of Germany ....... 4013077

[51] Int. Cl.$^5$ .............................. C12P 19/04
[52] U.S. Cl. .................... 435/101; 435/105; 435/207; 536/124; 530/395
[58] Field of Search ............ 435/105, 207, 101; 530/395; 536/124

[56] References Cited

U.S. PATENT DOCUMENTS

4,918,009  4/1990  Nilsson ............................. 536/4.1
4,963,469  10/1990  Mattes et al. ...................... 435/207

FOREIGN PATENT DOCUMENTS

0226563A1  6/1987  European Pat. Off. .

OTHER PUBLICATIONS

Kurt G. I. Nilsson, "Enzymatic Synthesis of Oligosaccharides", Trends in Biotechnology, Oct. 1988, vol. 6, No. 10, pp. 256–264.
Schachter, Clinical Biochemistry, 17, 3–13 (1984).
Sharon, Trends in Biochem. Sci., 9, 198–202 (1984).
Hakomori, Cancer Research, 45, 2405–2414 (1985).
Hakomori, Scientific American, 254, Supplement p. 32 (1986).
Li et al., Advanced Carbohydrate Chemistry and Biochemistry, 40, 235–286 (1982).
Auge et al., Carbohydrate Research, 193, 288–293 (1989).
Unverzagt et al., J. Am. Chem. Soc., 112, 9308–9309 (1990).
Wallenfels et al., The Enzymes, 3rd Edition, vol. VII, S. 617–663, (Boyer, editor, Acad. Press, New York 1972).
Barnett, Int. J. Biochem., 6, 321–328 (1975).
Peyrieras et al., The EMBO Journal, 2, 823–832 (1983).
Schwarz et al., Trends in Biochem. Sci., 9, 32–34 (1984).
Paulsen et al., *Liebigs Ann. Chem.* (1985), pp. 2028–2048.
Paulson et al., *Glycoconjugate Res.* (vol. 1), pp. 247–250.
Sato et al., *Tetrahedron Lett.* (1988), vol. 29(41), pp. 5267–5270.
Dill et al., *Carb. Res.*, vol. 142 (1985), pp. 11–20.
Toone et al., *Tetrahedron*, vol. 45(17), 1989, pp. 5365–5422.
Kunz, Angew. Chem., vol. 99 (1987), pp. 297–311.

*Primary Examiner*—Ronald W. Griffin
*Assistant Examiner*—Pamela S. Webber
*Attorney, Agent, or Firm*—Finnegan, Henderson, Farabow, Garret & Dunner

[57] ABSTRACT

It has been possible to show for a first time with the process according to the invention that the synthesis of glyco conjugates is possible by direct linkage of sugars with serine, serine derivatives and serine peptides with the aid of glucosidases.

8 Claims, No Drawings

PROCESS FOR THE GLYCOSIDASE-CATALYZED SYNTHESIS OF GLYCO CONJUGATES

Glyco conjugates (glycoproteins, glycosphingolipids, glycophospholipids) play a central part in biological recognition processes such as tumori genesis, bacterial and viral infection, cell-cell recognition, cell growth and cell differentiation. They form the basis for blood-group classification and are responsible for the internalization of various macromolecular substances and medicaments. An important area of use of glycoproteins is therefore, for example, the selective addressing of drugs to the target organ and the protection of medicaments from proteolytic breakdown (H. Schachter, Clinical Biochemistry 17, (1984) 3; N. Sharon, Trends Biochem.-Sci. 9 (1984) 198; S. Hakamori, Cancer Res. 45 (1985) 2405; S. Hakamori, Scientific American 254 (1986) No. 5, 32).

Given the background of the said functions of glyco conjugates, the synthesis thereof attracts particular interest.

The peptide and carbohydrate moieties in glycoproteins are usually linked together covalently. Despite the wide variety of structures, the linkage region is characteristic and varies only slightly. There are three main types of linkage in nature: the N-glycosidic linkage between N-acetylglucosamine and the amide functionality of asparagine, the a-O-glycosidic linkage between N-acetyl-galactosamine and the hydroxyl functionality of serine or threonine and the b-O-glycosidic linkage of xylose or galactose to various hydroxy amino acids.

Furthermore, b-O-glycosidic linkages of glucose to the serine-like ceramide moiety are found in some interesting glycosphingolipids. Ceramides are composed of sphingosine [(2S, 3R, 4E)-2-amino-4-octadecene-1,3-diol], dehydro-sphingosine (sphinganine) or phytosphingosine (4-D-hydroxysphinganine) which are acylated with long-chain fatty acids ($C_{14}$-$C_{26}$) on the 2-amino group (Y.-T. Li, S.-C. Li, Adv. Carbohydr. Chem. Biochem. 40 (1982) 235).

The central problems in chemical syntheses of glyco conjugates are thus the stereo- and regioselective serial connection of monosaccharide units to give oligosaccharides, the stereoselective formation of the glycosidic linkage to give the aglycone and, not least, the synthesis of the aglycone, for example of a peptide or ceramide.

The solution to these problems requires, even in relatively small glycopeptides, refined synthesis strategies with tailored protective group combinations from carbohydrate and peptide chemistry. Chemical glycoprotein syntheses are thus often multistage, time-consuming reactions which frequently provide only small amounts of the required substance free of all protective groups [H. Kunz, Angew. Chem. 99 (1987) 297–311); R.R. Schmidt in "Stereochemistry of Organic and Bioorganic Transformations", W. Bartmann and K.B. Sharpless, ed. p. 169, Verlag Chemie Weinheim (1987); H. Paulsen et al. Starch/Stärke 40 (1988) 465–472].

Enzymes from the biosynthesis of oligosaccharides are increasingly being used in the synthesis of these substances. The high stereo- and regioselectivities associated therewith, and the avoidance of elaborate protective group chemistry frequently make possible good yields compared with multistage chemical syntheses.

Now, for the first time, chemoenzymatic glycoprotein syntheses have been described recently [C. Augé, C. Gautheron and H. Pora, Carbohydr. Res. 288 (1989); J. Thiem and T. Wiemann, Angew. Chem. 102, 78 (1990); C. Unverzagt, H. Kunz and J.C. Paulson, J. Am. Chem. Soc. 112, 9308 (1990)]. These entail enzymatic glycosidation on the carbohydrate moiety, i.e. extension via a sugar-sugar linkage, of chemically synthesized conjugates of peptides or amino acids and a sugar.

The said enzymes which are used for forming the saccharidic linkages are glycosyltransferases. These are regarded as highly specific with regard to the glycosyl donor and the acceptor, and require activated sugars such as, for example, UDP-glucose for the glycosidation. However, the difficulty of obtaining the glycosyltrans-ferases and the activated sugars does not allow wide use in vitro or syntheses on a larger scale.

The preparative synthesis of glycopeptides (glyco conjugates) by enzymatic linkage of mono- or oligo-saccharides with an amino acid or a peptide has not to date been described either with transferases or with other enzymes [G.M. Whitesides et al., Tetrahedron 45 (1989), 5365–5422].

Glycosidases catalyze in natural systems the hydrolysis of glycosidic linkages. In recent years, glycosidases have increasingly been used by a reversal of the hydrolytic reaction—also for the preparative synthesis of glycosides (R. Wallenfels, R. Weil in "The Enzymes", 3. Ed.; Boyer, P.D. (Ed); Academic Press, New York 1972, Vol. VII, p. 618; J.E.G. Barnett, Int. J. Biochem. (1975) 321–328; G.M. Whitesides et al., Tetrahedron 45 (1989) 5365–5422; Kurt G. Nilsson, Trends in Biotechn. 1988, 256). The hydroxyl compounds employed as nucleophile are simple primary or secondary alcohols, some monosaccharides and, in a few cases, also steroids. The main disadvantages of these syntheses are the low yields and, in many cases, the formation of by-products.

It has now been found that D- and L-serine, and D- and L-serine derivatives can likewise function as good nucleophiles. This makes it possible for the first time to bring about in vitro the glycosidic linkage of hydroxy amino acids or their derivatives with monosaccharides using an enzyme not intended by nature for this class of product. It has thus been possible to show for the first time that glyco conjugates can be synthesized by direct linkage of sugars with D- and L-serine, D- and L-serin derivatives and D- and L-serine peptides with the aid of glycosidases. This is especially surprising because glycosidases are inhibited by N-containing monosaccharide analogs such as 1-deoxynojirimycin [N. Peyrieras et al., Embo J. 2, 823 (1983)], bicyclic N-containing compounds such as swainsonine [$8\alpha,\beta$-indolizidine-$1\alpha,$-$2\alpha,8\beta$-triol; R.T. Schwarz, R. Datema, Trends Biochem. Sci. 9, 32 (1984)], but also by simple N-containing alcohols such as ethanolamine [R. Wallenfels, R. Weil in "The Enzymes", 3. Ed.; Boyer, P.D. (Ed); Academic Press, New York 1972, Vol. VII, p. 618]. Thus, amino acids and their derivatives might also have been able to act as inhibitors.

In part, the resulting compounds correspond to partially protected natural glyco conjugates or, in particular, represent modifications of the latter and can be used as synthetic precursors for larger conjugates.

Thus the invention relates to a process for preparing glyco conjugates of the formula I

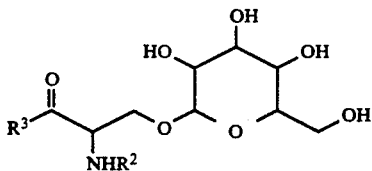

which comprises incubating the compound of the formula II

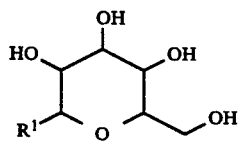

in which $R^1$ is fluorine, a hydroxyl group, an alkoxy group with 1 to 5 carbon atoms, an alkenyloxy group with 2 to 5 carbon atoms, an aryloxy group with 6 to 10 carbon atoms or a carbohydrate residue which is bonded via an oxygen atom, with the compound of the formula III

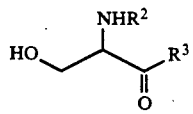

in which $R^2$ is an amino protective group and $R^3$ is a hydroxyl group, an alkoxy or alkylmercapto group or an alkenyloxy group, each of which has 1 to 18 carbon atoms and can be substituted by halogen or cyano, or an aryloxy group which has 6 to 10 carbon atoms and can be substituted by alkyl, alkoxy, alkylmercapto, in each case with 1 to 5 carbon atoms, and nitro groups, or the group —$NHR^4$ in which $R^4$ is an alkyl group with 1 to 5 carbon atoms or a radical of the formula IV

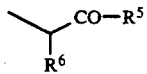

or a di- or tripeptide residue of the formula V or VI

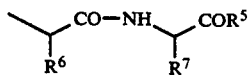

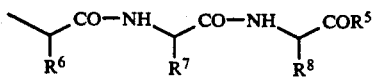

where $R^5$ is a hydroxyl group, an alkoxy, an alkylmercapto or an alkenyloxy group, each of which has 1 to 5 carbon atoms and can be substituted by halogen or cyano, or an aryloxy group which has 6 to 10 carbon atoms and can be substituted by alkyl, alkoxy, alkylmercapto, each of which has 1 to 5 carbon atoms, and nitro groups, and $R^6$, $R^7$ and $R^8$, which are identical or different, are hydrogen or straight-chain, branched or cyclic alkyl or alkenyl groups which have 1 to 10 carbon atoms and can be substituted by halogen, hydroxyl, alkoxy, mercapto, alkyl-mercapto, aryl or heteroaryl, in the presence of a glycosidase.

Glucose, galactose and mannose are possible and preferred for the compound of the formula II. A methoxy group is preferably employed as alkoxy group in the $R^1$ position of the formula II, and an allyloxy or vinyloxy group is preferably employed as alkenyloxy group. The aryloxy group can be substituted by electron-attracting substituents, for example nitro or cyano groups, or halogen. A phenoxy, an ortho- or para-nitrophenoxy or dinitrophenoxy group is preferably used. The saccharide formed by the carbohydrate residue in the $R^1$ position is preferably maltose or latose. $R^1$ is particularly preferably fluorine or para- or ortho-nitrophenoxy group.

It is essentially possible to employ as protective group in the $R^2$ position of the formula III the amino protective groups conventional in peptide and glycopeptide chemistry, such as, for example, acyl groups, including acyl radicals of long-chain fatty acids and alkyl- or aryloxy-carbonyl groups. Protective groups which can be used are described, for example, in the article by H. Hubbuch in Kontakte 3/79, page 14, in T.W. Greene, Protective Groups in Organic Synthesis, John Wiley & Sons 1981, p. 223 ff. or in Houben-Weyl, Vol. 15/1 p. 46. Preferably employed are benzyloxycarbonyl (Z), allyloxycarbonyl (Aloc) and tertiary-butyloxycarbonyl (Boc), as well as trichloro-ethoxycarbonyl, formyl, acetyl, chloroacetyl, trifluoro-acetyl, phenacetyl, benzoyl or acyl radicals of long-chain fatty acids with 6 to 24 carbon atoms.

The radical in the $R^3$ position and $R^5$ from formulae IV-VI are preferably methoxy, methoxymethyl, benzyloxymethyl, methylmercaptomethyl, ethoxy, chloroethoxy, bromoethoxy or cyanoethoxy, and vinyloxy groups and conventional carboxyl protective groups of peptide chemistry (Houben-Weyl Vol. 15/1, p. 315 ff.), such as, for example, benzyloxy, trichloroethoxy, p-nitrobenzyloxy, p-methoxybenzyloxy, piperonyloxy, allyloxy or tertiary-butyloxy and tertiary-butyldimethylsilyloxy groups.

When $R^3$ is the amino group $NHR^4$, $R^4$ is preferably the group of the formula IV and V in which $R^6$ and $R^7$, which are identical or different, are hydrogen or straight-chain, branched or cyclic alkyl or alkenyl groups which have 1 to 10 carbon atoms and can be substituted by halogen, hydroxyl, mercapto, alkoxy, alkylmercapto, aryl or heteroaryl. The substituents of $R^6$ and $R^7$ are essentially the side chains of neutral, aliphatic, aromatic or cyclic α-amino acids. Particularly preferably used as compound of the formula III are Z-Ser-Oallyl, Z-Ser-Ala-OMe, Z-Ser-Leu-OMe, Aloc-Ser-Gly-OEtCl, Boc-Ser-Oallyl and Aloc-Ser-Phe-OMe. When $R^2$ in the compound of the formula III is an acyl radical of long-chain fatty acids with 6 to 24 carbon atoms and $R^3$ is an alkoxy group with 6 to 18 carbon atoms, the compound of the formula III is a compound which is structurally similar to sphingosine or sphinganine, which are of interest as model substance for the glycosidase-catalyzed synthesis of glyco-sphingolipids.

The substrates of the formula II and III can either be bought (for example nitrophenyl glycosides) or easily prepared by methods known per se (glycosyl fluorides by the method of F. Micheel, A. Klemer, Adv. Carbohydr. Chem. 16, 85 (1961); German Offenlegungsschrift 30 40 805; German Offenlegungsschrift 34 32 565; amino acids and peptides, and protected derivatives by the methods in Houben-Weyl Volumes 15/I and 15/II).

The compounds of the formula II and of the formula III can be employed in the ratio of 4:1 to 1:10, preferably 3:2 to 1:4. 4 to 40 units of the enzyme are expediently used per mmol of glycosyl donor III.

The reaction can take place in a pH range from 5.0 to 8.0, but advantageously between pH 6.0 and 7.5. Buffers to be used are: HEPES, TRICIN, TAPS, MES, TES, and MOPS, CHES, TRIS, and potassium and sodium phosphate buffers. The molarity should be between 0.01 and 1.0, preferably between 0.01 and 0.1. Moreover, the temperature should be kept between about -30° C. and 50° C., preferably between 20° C. and 35° C. The enzyme increasingly undergoes irreversible inactivation as the temperature increases above 50° C. The incubation time can be from 1 to 30 hours.

Advantageously used are glucosidases from yeast and sweet almonds, galactosidases from *E. coli*, coffee beans, bovine testes and from *Aspergillus niger*, mannosidases from almonds, jack bean and snail acetone powder, amylases from *Aspergillus oryzae*, *Bacillus subtilis* and pig pancreas, amyloglucosidases from *Aspergillus niger* and a transglucosidase.

When the glycosyl donor is glucose or a 1-gluco-hexo-pyranoside, then it is particularly preferred to use glucosidase as enzyme. However, when galactose or a 1-galacto-hexopyranoside, or mannose or a 1-manno-hexo-pyranoside is employed, an enzyme to be used advantageously is galactosidase or mannosidase. Thus, whereas there is a relatively wide substrate specificity in the case of the glycosyl donor II, there is flexibility in the choice of the compound of the formula III. A large number of different N- and carboxyl-protective groups can thus be freely combined.

To improve the dissolution of the substrate II and III it is possible to use solvents which have no or only slight adverse effects on the activity of the enzyme. Examples of these are acetone, dimethoxyethane, diglyme, but especially diisopropyl and tert-butyl methyl ethers, toluene and xylene. It is also possible to increase the reaction rate by adding salts which are physiologically compatible with the enzymes used. Examples of such salts are $MnSO_4$, $CaCl_2$, KCl, NaBr, LiCl, LiBr and $KMnO_4$, but $NiSO_4$ and $MgCl_2$ are preferred.

The glycosidases used according to the invention can be employed as free water-soluble enzyme or in a form insoluble in water bound by conventional methods to a carrier (cf. German Offenlegungsschrift 27 32 301) in an aqueous solution. When the enzyme is used in immobilized form, this can take place both in batch and in continuous processes.

The progress of the reaction can be followed by HPLC [ODS-Hypersil 5 μm 4.6×250 mm, MeOH-$H_2O$, Bioselect 100/10-18 250×4.6 mm, $CH_3CN$-$H_2O$-] or by TLC [$CHCl_3$/Hex/ MeOH=3:1:1].

The subsequent working up is carried out, for example, by extraction with toluene or diisopropyl ether, treatment with XAD adsorbents (for example XAD-2) to remove nitro-phenol, freeze-drying of the aqueous phase and purification by chromatography, for example preparative thin-layer chromatography, chromatography on silica gel (flash or conventional), flash chromatography or MPLC on Eurosil Bioselect 100-30 C18 (Knauer) or LiChroPrep RP 18 (Merck) and chromatography on Sephadex LH20 (Pharmacia) or Biogel P2 100-200 mesh (BioRad). It is also possible first to freeze-dry the reaction solution and then to extract the solid residue with methanol, in which case filtration and concentration of the methanolic solution may be followed by use of the above-mentioned chromatographic methods for the further purification.

The examples listed below serve to explain the invention further.

EXAMPLE 1

75 U of β-galactosidase from E. coli (50 μl of $(NH_4)_2SO_4$ suspension, Boehringer Mannheim) are added to 1.24 g (4.1 mmol) of ortho-nitrophenyl β-galactoside and 2.0 g (7.5 mmol) of (L)-Z-serine ethyl ester in 100 ml of potassium phosphate buffer (0.1 M, pH=7; 10 mM $MgCl_2$), and the mixture is stirred at room temperature for 5 h. Freeze-drying, extraction of the residue with methanol, subsequent flashchromatography on silica gel (MeOH/$CH_2Cl_2$/ hexane=1:6:6) and final purification by preparative thin-layer chromatography (MeOH/$CHCl_3$/hexane=2:6:6) result in 300 mg (17%) of the required glyco conjugate which, according to $^1H/^{13}C$-NMR, is a pure compound: $^{13}C$-NMR (DMSO-$d_6$, 75 MHz, δ in ppm): Cl (Gal): 104.03 (β) FAB-MS: $MH^+$=430

EXAMPLE 2

150 U of β-galactosidase from *E. coli* (100 μl of $(NH_4)_2SO_4$ suspension, Boehringer Mannheim) are added to 2.5 g (8.3 mmol) of ortho-nitrophenyl β-galactoside and 8.0 g (28.7 mmol) of (L)-Z-serine allyl ester in 200 ml of potassium phosphate buffer (0.07 M, pH =7; 10 mM $MgCl_2$), and the mixture is stirred at room temperature for 24 h. Working up by freeze-drying, extraction of the residue with methanol and column chromatography on silica gel (MeOH/$CH_2Cl_2$/hexane=1:6:2) yields 435 mg (12%) of the required glyco conjugate.
$^{13}C$-NMR (DMSO-$d_6$, 75 MHz, δ in ppm):
Cl (Gal): 104.06 (β)
FAB-MS: $MH^+$=442

EXAMPLE 3

124 mg (0.41 mmol) of ortho-nitrophenyl β-galactoside and 200 mg (0.72 mmol) of (L)-Z-serine allyl ester are stirred with 7.5 U of β-galactosidase from E. coli (5 μl of $(NH_4)_2SO_4$ suspension, Boehringer Mannheim) in 10 ml of potassium phosphate buffer (0.07 M, pH 7.0; 10 mM $MgCl_2$), at 50° C. for 2¼ h. Freeze-drying and preparative thin-layer chromatography (MeOH/$CHCl_3$/hexane=2:2:6) yield 22 mg (12%) of the expected glycoside.

The spectroscopic data correspond to Example 2.

EXAMPLE 4

225 mg (0.85 mmol) of ortho-nitrophenyl β-galactoside and 500 mg (1.8 mmol) of (L)-Z-serine allyl ester are stirred with 15 U of β-galactosidase from E. coli (10 μl of $(NH_4)_2SO_4$ suspension, Boehringer Mannheim) in 20 ml of potassium phosphate buffer (0.07 M, pH 7.0; 10 mM $MgCl_2$), at room temperature for 2¼ h. Freeze-drying and extraction of the residue with methanol is followed by chromatography on Sephadex LH20 (column 60×2.5 cm) with methanol. 34 mg (9%) of the required product are obtained.

The spectroscopic data correspond to Example 2.

EXAMPLE 5

75 U of β-galactosidase from E. coli (50 μl of $(NH_4)_2SO_4$ suspension, Boehringer Mannheim) are added to 538 mg (1.78 mmol) of ortho-nitrophenyl β-galactoside and 1.07 g (3.84 mmol) of (D)-Z-serine allyl ester in 50 ml of TRIS buffer (0.1 M, pH=7.2), and the mixture is stirred at room temperature for 6.5 h. Freeze-drying is followed by chromatography on Biogel P2

(100-200 mesh, column 50×3 cm) with water and on silica gel with MeOH/CHCl₃/hexane 1:3:1. The required glyco conjugate is obtained in a yield of 95 mg (12%).

¹³C-NMR (DMSO-d₆, 75 MHz, δ in ppm): FAB-MS: MH⁺=442

EXAMPLE 6

75 U of β-galactosidase from *E. coli* (50 μl of (NH₄)₂SO₄ suspension, Boehringer Mannheim) are added to 542 mg (1.8 mmol) of ortho-nitrophenyl β-galactoside and 1.06 g (3.8 mmol) of (L)-Z-serine ethyl ester in 50 ml of TRIS buffer (0.01 M, pH=7.2.), and the mixture is stirred at room temperature for 5.5 h. Subsequent purification is carried out by freeze-drying, chromatography with water on Biogel P2 (100-200 mesh, column 50×3 cm) and with CHCl₃/MeOH/hexane (3:1:1) on silica gel. 78 mg of the required glycoside are obtained (10% yield).

The spectroscopic data correspond to Example 1.

EXAMPLE 7

532 mg (1.77 mmol) of ortho-nitrophenyl β-galactoside and 1.02 g (4.16 mmol) of (L)-Boc-serine allyl ester are stirred with 75 U of β-galactosidase from *E. coli* (50 μl of (NH₄)₂SO₄ suspension, Boehringer Mannheim) in 50 ml of TRIS buffer (0.01 M, pH=7.2) at room temperature for 5.5 h. Freeze-drying, chromatography with water on Biogel P2 (100-200 mesh, column 50×3 cm) and with CHCl₃/MeOH/ hexane (3:1:1) on silica gel yield 130 mg (18%) of the required glyco conjugate.

The compound is pure according to TLC ¹H/¹³C-NMR and FAB-MS.

¹³C-NMR (DMSO-d₆, 75 MHz, δ in ppm):
Cl (Gal) 104.01 (β)
FAB-MS: MH⁺=408

EXAMPLE 8

391 mg (1.3 mmol) of p-nitrophenyl α-mannoside and 714 mg (2.9 mmol) of (L)-Z-serine allyl ester are stirred with 22 U (220 μl of (NH₄)₂SO₄ suspension) of α-mannosi-dase (from jack beans, Sigma) in 35 ml of Tris buffer (pH 6, 0.01 M) at room temperature for 3.5 h. Freeze-drying and chromatography on 90 g of Emosil-Bioselect (100–30 C18 in acetonitrile/water 40:60) and silica gel (CHCl₃/methanol/ hexane 3:1:1) result in 22 g (4%) of the required product, which is pure according to ¹H/¹³C-NMR and FAB-MS.

¹³C-NMR (DMSO-d₆, 75 MHz, δ in ppm):
Cl (Man): 100.61 (β)
FAB-MS: MH⁺=442

| Example | Compound of the formula II | Compound of formula III R² | R³ (*) | Enzyme Type | [units] | Amount [mmol] II | III | Buffer (**) [ml] | Time/temp. | Yield [%] | Working up in analogy to Example |
|---|---|---|---|---|---|---|---|---|---|---|---|
| 9 | α-F-Glc | Z | Oallyl | A | 8.4 | 0.7 | 0.80 | 10 | 7 h, RT | 5 | 1 |
| 10 | (R¹ = F) | Z | Oallyl | B | 2.5 | 0.75 | | 10 | 21 h, RT | 2 | 1 |
| 11 | | Z | Oallyl | C | 500 | 2.5 | 0.75 | 10 | 21 h, RT | 2 | 1 |
| 12 | ortho-nitro-phenyl β-galactoside | Ac | Oheptyl | C | 500 | 2.5 | 0.75 | 10 | 21 h, RT | 12 | 8 |
| 13 | | Z | Oallyl | D | 15 | 0.42 | 1.54 | 10 | 3 h, RT | 9 | 5 |
| 14 | | Z | Oallyl | D | 15 | 0.42 | 0.72 | 10 | 2 h, RT | 12 | 5 |
| 15 | | Z | Oallyl | D | 1.5 | 0.42 | 1.4 | 10 | 25 h, RT | 6 | 5 |
| 16 | | Z | Oallyl | D | 7.5 | 0.42 | 0.72 | 10 | 2.5 h, RT | 8 | 5 |
| 17 | | Z | Oallyl | D | 7.5 | 0.42 | 0.72 | 5 + 5 ml toluene | 4 3/4 h, RT | 6 | 5 |
| 18 | | Z | Oallyl | D | 7.5 | 0.42 | 0.72 | 5 + 5 ml xylene | 4 3/4 h, RT | 8 | 5 |
| 19 | | Ac | Oallyl | D | 75 | 4.2 | 1.8 | 50 ml (***) | 5.5 h, RT | 19 | 5 |
| 20 | | Z | OMe | D | 225 | 4.2 | 16.0 | 100 | 6 h, RT | 10 | 5 |
| 21 | | Aloc | OBn | D | 7.5 | 0.4 | 0.8 | 10 | 21 h, RT | 5 | 8 |
| 22 | | Aloc | OEtBr | D | 7.5 | 0.4 | 0.8 | 10 | 6 h, RT | 2 | 1 |
| 23 | | Z | LeuOMe | D | 7.5 | 0.4 | 0.7 | 10 | 7 h, RT | 5 | 3 |
| 24 | | Aloc | PheOMe | D | 7.5 | 0.4 | 0.7 | 10 | 6 h, RT | 2 | 3 |
| 25 | p-nitrophenyl β-mannoside | Z | Oallyl | E | 0.5 | 0.03 | 0.09 | 2 | 170 h, RT | 2 | 3 |

(*) Compound of the L series
(**) Unless otherwise indicated: potassium phosphate buffer (0.07M; pH = 7; 10 mM MgCl₂)
(***) TRIS buffer (0.1M, pH = 7.2)
A: α-Glucosidase (maltase) from yeast, EC 3.2.1.20 from Boehringer Mannheim
B: Transglucosidase from Amano Pharmaceutical Co.
C: α-Amylase from *Aspergillus oryzae*, EC 3.2.1.1, from Sigma Chemie GmbH
D: β-Galactosidase from *E. coli* EC 3.2.1.23 from Boehringer Mannheim
E: β-Mannosidase, snail acetone powder, EC 3.2.1.25 from Sigma Chemie GmbH

We claim:
1. Process for preparing glyco conjugates of the formula I

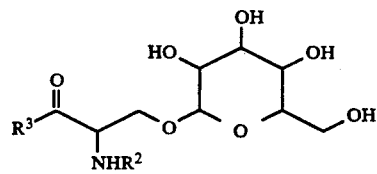

which comprises incubating the compound of the formula II

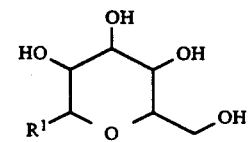

in which R¹ is fluorine, a hydroxyl group, an alkoxy group with 1 to 5 carbon atoms, an alkenyloxy group with 2 to 5 carbon atoms, an aryloxy group with 6 to 10 carbon atoms or a carbohydrate residue which is bonded via an oxygen atom, with the compound of the formula III

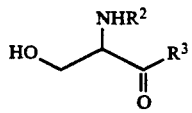

in which R² is an amino protective group and R³ is a hydroxyl group, an alkoxy or alkylmercapto group or an alkenyloxy group, each of which has 1 to 18 carbon atoms and can be substituted by halogen or cyano, or an aryloxy group which has 6 to 10 carbon atoms and can be substituted by alkyl, alkoxy, alkylmercapto, in each case with 1 to 5 carbon atoms, and nitro groups, or the group —NHR⁴ in which R⁴ is an alkyl group with 1 to 5 carbon atoms or a radical of the formula IV

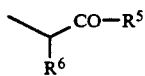

or a di- or tripeptide residue of the formula V or VI

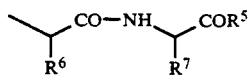

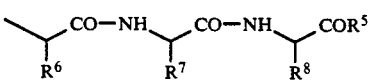

where R⁵ is a hydroxyl group, an alkoxy, an alkylmercapto or an alkenyloxy group, each of which has 1 to 5 carbon atoms and can be substituted by halogen or cyano, or an aryloxy group which has 6 to 10 carbon atoms and can be substituted by alkyl, alkoxy, alkylmercapto, each of which has 1 to 5 carbon atoms, and nitro groups, and R⁶, R⁷ and R⁸, which are identical or different, are hydrogen or straight-chain, branched or cyclic alkyl or alkenyl groups which have 1 to 10 carbon atoms and can be substituted by halogen, hydroxyl, alkoxy, mercapto, alkyl-mercapto, aryl or heteroaryl, in the presence of a glycosidase.

2. The process as claimed in claim 1, wherein the compound of the formula II in which R¹ is fluorine, a methoxy group, an allyloxy group, a vinyloxy group, a phenoxy group, an ortho- or para-nitrophenoxy group or a dinitrophenoxy group is employed.

3. The process as claimed in claim 1, wherein the compound of the formula III in which R² is benzyloxycarbonyl, allyloxycarbonyl, tertiary-butyloxycarbonyl, formyl, acetyl, chloroacetyl, trifluoroacetyl, phenacetyl, benzoyl or an acyl radical of a long-chain fatty acid with 6 to 24 carbon atoms is employed.

4. The process as claimed in claim 1 or 3, wherein the compound of the formula III in which R³ is methoxy, methoxymethyl, benzyloxymethyl, methylmercaptomethyl, ethoxy, chloroethoxy, bromoethoxy or cyanoethoxy, benzyloxy, p-nitrobenzyloxy, p-methoxybenzyloxy, piperonyloxy, allyloxy or vinyloxy and tertiary-butyloxy or tertiary-butyldimethylsilyloxy or, when R³ is the group NHR⁴, R⁴ is the group of the formula IV or V in which R⁵ has the meaning as defined for R³, it being possible for R³ and R⁵ to be identical or different, is employed.

5. The process as claimed in claim 1, wherein the compounds of the formula II and of the formula III are employed in the ratio 4:1 to 1:10.

6. The process as claimed in claim 1, wherein the reaction takes place in a pH range from 5.0 to 8.0.

7. The process as claimed in claim 1, wherein the reaction takes place in a temperature range from −30° to 50° C.

8. The process as claimed in claim 1, wherein the glucosidase from yeast and sweet almonds, galactosidase from *E. coli, Aspergillus* niger, coffee beans or bovine testes, β-mannosidase in the form of snail acetone powder or α-mannosidase from jackbeans or almonds, amylase from *Aspergillus oryzae, Bacillus subtilis* or pig pancreas or amyloglucosidases from *Aspergillus niger* are employed as glucosidase.

* * * * *